(12) United States Patent
Asfora

(10) Patent No.: US 12,207,828 B2
(45) Date of Patent: *Jan. 28, 2025

(54) PARALLEL GUIDE FOR ACCESS NEEDLE

(71) Applicant: Asfora IP, LLC, Sioux Falls, SD (US)

(72) Inventor: Wilson T. Asfora, Miami, FL (US)

(73) Assignee: Asfora IP, LLC, Sioux Falls, SD (US)

( * ) Notice: Subject to any disclaimer, the term of this patent is extended or adjusted under 35 U.S.C. 154(b) by 277 days.

This patent is subject to a terminal disclaimer.

(21) Appl. No.: 18/049,157

(22) Filed: Oct. 24, 2022

(65) Prior Publication Data

US 2023/0145974 A1 May 11, 2023

Related U.S. Application Data

(63) Continuation of application No. 16/932,285, filed on Jul. 17, 2020, now Pat. No. 11,478,260.

(51) Int. Cl.
| | |
|---|---|
| *A61B 17/17* | (2006.01) |
| *A61B 17/16* | (2006.01) |
| *A61F 2/30* | (2006.01) |

(52) U.S. Cl.
CPC .......... *A61B 17/17* (2013.01); *A61B 17/1633* (2013.01); *A61B 17/1728* (2013.01);
(Continued)

(58) Field of Classification Search
CPC .................................................. A61B 17/1757
See application file for complete search history.

(56) References Cited

U.S. PATENT DOCUMENTS 3,110,092 A * 11/1963 Bechtold ............... B22F 3/1028
75/235
3,389,456 A * 6/1968 Ishizuka ................. B23P 15/00
29/441.1
(Continued)

FOREIGN PATENT DOCUMENTS

| | | |
|---|---|---|
| RU | 2489983 C1 | 8/2013 |
| WO | 2014149746 A1 | 9/2014 |

OTHER PUBLICATIONS

Sicage System Surgical Technique Brochure, 2017, [online], [site visited Mar. 18, 2019]. Retrieved fromurl:http://sicage.com/wp-content/uploads/2018/01/ED0016RA_Final.pdf (Year: 2017).
(Continued)

*Primary Examiner* — Christian A Sevilla
(74) *Attorney, Agent, or Firm* — Fox Rothschild LLP

(57) ABSTRACT

A parallel spacer for parallel spacing of a plurality of guiding elements during surgery is provided. The parallel spacer includes a parallel spacer body defining a first guide aperture extending through the parallel spacer body, the first guide aperture being sized to receive a first guiding element in a first orientation with respect to the parallel spacer body and hold the guiding element at the first orientation. The body further defines a second guide aperture extending through the parallel spacer body, sized to receive an access needle. The parallel spacer further includes a first external positioning protrusion, with the first guide aperture extending through the first external positioning protrusion, and a second external positioning protrusion, with the second guide aperture extending therethrough. The second guide aperture is open from a proximal end of the parallel spacer body to a distal end of the second external positioning protrusion.

12 Claims, 15 Drawing Sheets

(52) U.S. Cl.
  CPC ...... *A61B 17/1757* (2013.01); *A61F 2/30988* (2013.01); *A61F 2002/30995* (2013.01)

(56) References Cited

U.S. PATENT DOCUMENTS

| | | | |
|---|---|---|---|
| 4,129,945 A * | 12/1978 | Eibofner | A61C 1/14 |
| | | | 279/903 |
| 4,196,506 A | 4/1980 | Reed | |
| 4,354,840 A * | 10/1982 | Weissman | A61C 1/082 |
| | | | 433/25 |
| 4,486,689 A | 12/1984 | Davis | |
| 4,487,357 A * | 12/1984 | Simon | B21C 23/14 |
| | | | 72/266 |
| 4,563,727 A | 1/1986 | Curiel | |
| 4,917,111 A | 4/1990 | Pennig | |
| 5,100,404 A | 3/1992 | Hayes | |
| D326,156 S | 5/1992 | Martinez | |
| 5,144,946 A | 9/1992 | Weinberg et al. | |
| 5,147,367 A | 9/1992 | Ellis | |
| D337,820 S | 7/1993 | Hooper | |
| 5,324,295 A | 6/1994 | Shapiro | |
| D357,534 S * | 4/1995 | Hayes | D24/140 |
| 5,676,545 A | 10/1997 | Jones | |
| D389,639 S | 1/1998 | Priebe | |
| 5,725,581 A | 3/1998 | Branemark | |
| 5,727,958 A | 3/1998 | Chen | |
| 5,735,898 A | 4/1998 | Branemark | |
| D395,082 S | 6/1998 | Edgson | |
| 5,820,536 A | 10/1998 | Sato | |
| D406,642 S | 3/1999 | Remes | |
| D420,686 S | 2/2000 | Kunema | |
| 6,135,772 A | 10/2000 | Jones | |
| 6,149,686 A | 11/2000 | Kuslich et al. | |
| 6,270,503 B1 | 8/2001 | Schmieding | |
| 6,287,343 B1 | 9/2001 | Kuslich et al. | |
| 6,342,055 B1 | 1/2002 | Eisermann | |
| 6,391,058 B1 | 5/2002 | Kuslich et al. | |
| 6,517,542 B1 | 2/2003 | Papay et al. | |
| 6,554,830 B1 | 4/2003 | Chappius | |
| 6,565,572 B2 | 5/2003 | Chappius | |
| 6,604,945 B1 | 8/2003 | Jones | |
| 6,755,835 B2 | 6/2004 | Schultheiss et al. | |
| D560,727 S | 1/2008 | Denoual | |
| 7,354,442 B2 | 4/2008 | Sasso et al. | |
| D588,211 S | 3/2009 | Croston | |
| D596,758 S | 7/2009 | Constable | |
| 7,575,572 B2 | 8/2009 | Sweeney | |
| 7,608,062 B2 | 10/2009 | Sweeney | |
| 7,658,879 B2 | 2/2010 | Solar | |
| 7,717,947 B1 | 5/2010 | Wilberg et al. | |
| D626,615 S | 11/2010 | Isbrandt | |
| D629,517 S | 12/2010 | Jauch | |
| D634,428 S | 3/2011 | Anderson | |
| 8,052,688 B2 * | 11/2011 | Wolf | A61B 5/4836 |
| | | | 606/104 |
| 8,062,270 B2 | 11/2011 | Sweeney | |
| D667,548 S | 9/2012 | Brannon | |
| 8,303,602 B2 | 11/2012 | Biedermann et al. | |
| 8,382,808 B2 | 2/2013 | Wilberg et al. | |
| D678,187 S | 3/2013 | Huang | |
| D686,491 S | 7/2013 | Kuo | |
| 8,535,319 B2 | 9/2013 | Ball | |
| D691,201 S | 10/2013 | Roth | |
| 8,574,273 B2 | 11/2013 | Russell et al. | |
| D705,719 S | 5/2014 | Wong | |
| D708,191 S | 7/2014 | An | |
| 8,808,337 B2 | 8/2014 | Sweeney | |
| D714,765 S | 10/2014 | Goransson | |
| 8,870,836 B2 | 10/2014 | Sweeney | |
| 8,911,445 B2 | 12/2014 | Rocci | |
| 8,956,369 B2 | 2/2015 | Millett et al. | |
| D736,380 S | 8/2015 | Van Dalen | |
| 9,131,970 B2 | 9/2015 | Kang | |
| 9,138,245 B2 | 9/2015 | Mebarak | |
| 9,173,692 B1 | 11/2015 | Kaloostian | |
| D745,969 S | 12/2015 | Matheny | |
| 9,198,702 B2 | 12/2015 | Biedermann et al. | |
| D748,786 S | 2/2016 | Bailey | |
| 9,271,742 B2 | 3/2016 | Asfora | |
| 9,271,743 B2 | 3/2016 | Asfora | |
| 9,295,488 B2 | 3/2016 | Asfora | |
| 9,326,779 B2 | 5/2016 | Dorawa et al. | |
| 9,326,801 B2 | 5/2016 | Poulos | |
| 9,333,018 B2 | 5/2016 | Russell et al. | |
| 9,408,705 B2 | 8/2016 | Oosthuizen | |
| D767,042 S | 9/2016 | Martin | |
| 9,445,852 B2 | 9/2016 | Sweeney | |
| 9,445,909 B2 | 9/2016 | Cohen | |
| 9,504,526 B2 | 11/2016 | Hanson | |
| 9,526,548 B2 | 12/2016 | Asfora | |
| D778,156 S | 2/2017 | Follett | |
| 9,566,100 B2 | 2/2017 | Asfora | |
| 9,616,205 B2 | 4/2017 | Nebosky et al. | |
| 9,642,656 B2 | 5/2017 | Kotuljac et al. | |
| D790,964 S | 7/2017 | Akana | |
| D802,536 S | 11/2017 | Shang | |
| 9,826,993 B2 | 11/2017 | Bake et al. | |
| 9,826,994 B2 | 11/2017 | Eash | |
| D804,334 S | 12/2017 | Becker | |
| 9,855,063 B2 | 1/2018 | Feibel | |
| 9,907,582 B1 | 3/2018 | Olea | |
| D831,479 S | 10/2018 | Lylyk | |
| 10,111,650 B2 | 10/2018 | Nel | |
| D847,336 S | 4/2019 | Asfora | |
| D850,616 S | 6/2019 | Asfora | |
| D860,450 S | 9/2019 | Asfora | |
| 10,456,207 B2 * | 10/2019 | Flatt | A61B 17/162 |
| 10,603,054 B2 | 3/2020 | Asfora et al. | |
| 2001/0027152 A1 | 10/2001 | Bolledi | |
| 2002/0143343 A1 | 10/2002 | Castro | |
| 2003/0236527 A1 | 12/2003 | Kawakami | |
| 2004/0049284 A1 | 3/2004 | German | |
| 2004/0049286 A1 | 3/2004 | German | |
| 2004/0121890 A1 | 6/2004 | Taga et al. | |
| 2004/0230197 A1 | 11/2004 | Tornier | |
| 2005/0055026 A1 | 3/2005 | Biedermann et al. | |
| 2005/0071008 A1 | 3/2005 | Kirschman | |
| 2005/0149045 A1 * | 7/2005 | Elliott | A61B 17/17 |
| | | | 606/96 |
| 2005/0203532 A1 | 9/2005 | Ferguson | |
| 2005/0228398 A1 | 10/2005 | Rathbun et al. | |
| 2006/0107797 A1 * | 5/2006 | Bader | B25B 23/0064 |
| | | | 81/54 |
| 2006/0192319 A1 | 8/2006 | Solar | |
| 2006/0195111 A1 | 8/2006 | Couture | |
| 2006/0200248 A1 | 9/2006 | Beguin | |
| 2007/0000122 A1 | 1/2007 | Caya et al. | |
| 2007/0106305 A1 | 5/2007 | Kao et al. | |
| 2007/0233123 A1 | 10/2007 | Ahmad et al. | |
| 2008/0027458 A1 | 1/2008 | Aikins et al. | |
| 2008/0086144 A1 | 4/2008 | Zander | |
| 2008/0114370 A1 | 5/2008 | Schoenefeld | |
| 2008/0133020 A1 | 6/2008 | Blackwell | |
| 2008/0161820 A1 | 7/2008 | Wack | |
| 2009/0004625 A1 * | 1/2009 | Esposti | A61C 1/082 |
| | | | 433/165 |
| 2009/0024131 A1 | 1/2009 | Metzger | |
| 2009/0118736 A1 | 5/2009 | Kreuzer | |
| 2010/0137873 A1 | 6/2010 | Grady, Jr. | |
| 2010/0217399 A1 | 8/2010 | Groh | |
| 2011/0040303 A1 | 2/2011 | Iannotti | |
| 2011/0130795 A1 | 6/2011 | Ball | |
| 2011/0137352 A1 | 6/2011 | Biedermann et al. | |
| 2011/0213426 A1 | 9/2011 | Yedlicka et al. | |
| 2012/0089195 A1 | 4/2012 | Yedlicka et al. | |
| 2012/0136365 A1 | 5/2012 | Iannotti | |
| 2012/0197261 A1 | 8/2012 | Rocci | |
| 2012/0253353 A1 | 10/2012 | McBride | |
| 2012/0310361 A1 | 12/2012 | Zubok | |
| 2013/0065698 A1 | 3/2013 | Biedermann et al. | |
| 2013/0190570 A1 | 7/2013 | Hirsch | |
| 2013/0245602 A1 | 9/2013 | Sweeney | |
| 2013/0267958 A1 | 10/2013 | Iannotti | |
| 2013/0267960 A1 | 10/2013 | Groh | |

(56) References Cited

U.S. PATENT DOCUMENTS

| | | |
|---|---|---|
| 2013/0296864 A1* | 11/2013 | Burley .................. A61B 17/17 606/80 |
| 2014/0012340 A1 | 1/2014 | Beck et al. |
| 2014/0046381 A1 | 2/2014 | Asfora |
| 2014/0142643 A1 | 5/2014 | Bake |
| 2014/0236242 A1 | 8/2014 | Robinson |
| 2014/0243837 A1 | 8/2014 | Mebarak |
| 2014/0276857 A1 | 9/2014 | Major |
| 2014/0277165 A1 | 9/2014 | Katzman et al. |
| 2014/0277188 A1 | 9/2014 | Poulos |
| 2015/0157337 A1 | 6/2015 | Wolf |
| 2015/0157379 A1 | 6/2015 | Matsuzaki |
| 2015/0230844 A1 | 8/2015 | Ellis |
| 2015/0272597 A1 | 10/2015 | Johannaber |
| 2015/0272646 A1 | 10/2015 | Russell |
| 2015/0313658 A1 | 11/2015 | Kolb |
| 2015/0320469 A1 | 11/2015 | Biedermann et al. |
| 2016/0000489 A1 | 1/2016 | Kaloostian |
| 2016/0008044 A1 | 1/2016 | Sweeney |
| 2016/0089163 A1 | 3/2016 | Eash et al. |
| 2016/0143671 A1 | 5/2016 | Jimenez |
| 2016/0143742 A1 | 5/2016 | Asfora |
| 2016/0151100 A1 | 6/2016 | Biedermann et al. |
| 2016/0183995 A1* | 6/2016 | Zrinski .............. A61B 17/1728 606/96 |
| 2016/0220291 A1 | 8/2016 | Russell et al. |
| 2016/0310188 A1 | 10/2016 | Marino et al. |
| 2017/0181759 A1 | 6/2017 | Bouduban |
| 2018/0072488 A1 | 3/2018 | Benoit |
| 2018/0185038 A1 | 7/2018 | Hero |
| 2019/0125370 A1 | 5/2019 | Asfora |
| 2019/0125408 A1 | 5/2019 | Asfora et al. |
| 2020/0315637 A1 | 10/2020 | Asfora et al. |

OTHER PUBLICATIONS

International Search Report and Written Opinion for International Application No. PCT/US21/41600, filed Jul. 14, 2021, mailed Oct. 21, 2021.

65mm Flat Semi Circle Silicone Necklace Mold PM04, No. date available, online, site visited Feb. 1, 2019, retrieved fromurl:https://www.makememoldme.com/listing/588778232/65mm-flat-semi-circle-- silicone-mold (2019).

Citrus Slice by faberdasher, Aug. 17, 2016 online, site visited Feb. 1, 2019, retrieved from url:https://www.thingiverse.com/thing:1721009 (2016).

Silicone mold 8.times.3.5 mm lenses 10 pcs, earliest review Nov. 27, 2016, online, site visited Feb. 1, 2019, retrieved from url:https://www.etsy.com/listing/257627215/silicone-mold-8-x-35-mm-lenses- -10-pcs?ref=shop_review (2016).

CFR Peeek Fracture Fixation Plates, No. date available, [online], [site visited Oct. 25, 2018]. Retrieved fromurl:http:/ astoninspired.com/portfolio/cfr-peek-fracture-fixation-plates-- by-zubin-rao (Year: 2018).

* cited by examiner

PARALLEL GUIDE FOR ACCESS NEEDLE

CROSS-REFERENCE TO RELATED APPLICATIONS

The present application is a continuation of U.S. patent application Ser. No. 16/932,285, filed Jul. 17, 2020, which is incorporated herein by reference in its entirety.

TECHNICAL FIELD

The present invention relates generally to orthopedic surgery. More specifically, techniques, devices, and systems associated with the parallel implantation of a bone screw for joint fusion are described.

BACKGROUND

Stress across joints and in particular the sacroiliac joint generally is a common cause of pain including lower back pain. Various types of sacroiliac joint stress, including sacroiliac joint disruptions (i.e., separations) and degenerative sacroiliitis (i.e., inflammation) can result from lumbar fusion, trauma, postpartum, heavy lifting, arthritis, or unknown causes. Sacroiliac joint fixation or arthrodesis is sometimes recommended for skeletally mature patients with severe, chronic sacroiliac joint pain or acute trauma in the sacroiliac joint.

Conventional solutions for stabilizing joints and relieving pain in joints typically include the insertion of an implant, such as a metal screw, rod or bar, laterally across the joint. As multiple implants may be inserted across the joint, the relative orientation between the implants needs to be controlled. Guides that utilize a sliding mechanism are known. But such guides do not provide both flexibility and the control of discrete placement of the guides used for locating implants.

SUMMARY

According to an aspect of the present disclosure, a parallel spacer for parallel spacing of a plurality of guiding elements during surgery is provided. The parallel spacer includes a parallel spacer body having a proximal surface and a distal surface. The body defines a first guide aperture extending through the parallel spacer body between an opening in the proximal surface and an opening in the distal surface and defined by an internal wall, the first guide aperture being sized to receive a first guiding element in a first orientation with respect to the parallel spacer body and hold the guiding element at the first orientation. The body further defines a second guide aperture extending through the parallel spacer body between an opening in the proximal surface and an opening in the distal surface and defined by internal walls, sized to receive an access needle. The parallel spacer further includes a first external positioning protrusion extending distally from the distal surface of the parallel spacer body, with the first guide aperture extending through the first external positioning protrusion, and a second external positioning protrusion extending distally from the distal surface of the parallel spacer body, with the second guide aperture extending therethrough. An inner surface of the second guide aperture defines the second guide aperture, the second guide aperture is open from a proximal end of the parallel spacer body to a distal end of the second external positioning protrusion and is configured to receive or extract therefrom the second access needle.

According to various embodiments, the first guide aperture aligns to a first axis, and the second guide aperture aligns to a second axis.

According to various embodiments, the second guide aperture is open from the proximal end of the parallel spacer body to the distal end of the second external positioning protrusion is a direction radial to the first axis.

According to various embodiments, the second guide aperture is open from the proximal end of the parallel spacer body to the distal end of the second external positioning protrusion is a direction radial to the second axis.

According to various embodiments, the first axis and the second axis are parallel.

According to various embodiments, the second guide aperture is disposed to hold the second guiding element at a distance from the first guiding element.

According to various embodiments, the second guide aperture narrows toward the distal end of the second external positioning protrusion.

According to various embodiments, the first external positioning protrusion is configured to fit within at least one of a drill guide or tissue protector.

According to various embodiments, the inner surface of the second guide aperture includes a proximal portion, a distal portion that is narrower than the proximal portion, and a step between the proximal and distal portions, such that the proximal and distal portions and the step collectively define the narrowing secondary aperture.

According to various embodiments, a system is presented for parallel spacing a plurality of guiding elements during surgery. The system includes a tissue protector positioned over a first guiding element, a parallel spacer mounted to the tissue protector, and an access needle having a shape corresponding to the second guide aperture. The first external positioning protrusion is configured to be inserted into a portion of the tissue protector.

According to various embodiments, the second guide aperture is configured to align the access needle with an axis of the first aperture.

According to various embodiments, the tissue protector defines a bore extending completely therethrough, and the second guide element is receivable within an end of the bore.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which:

DETAILED DESCRIPTION

Figure 1A:
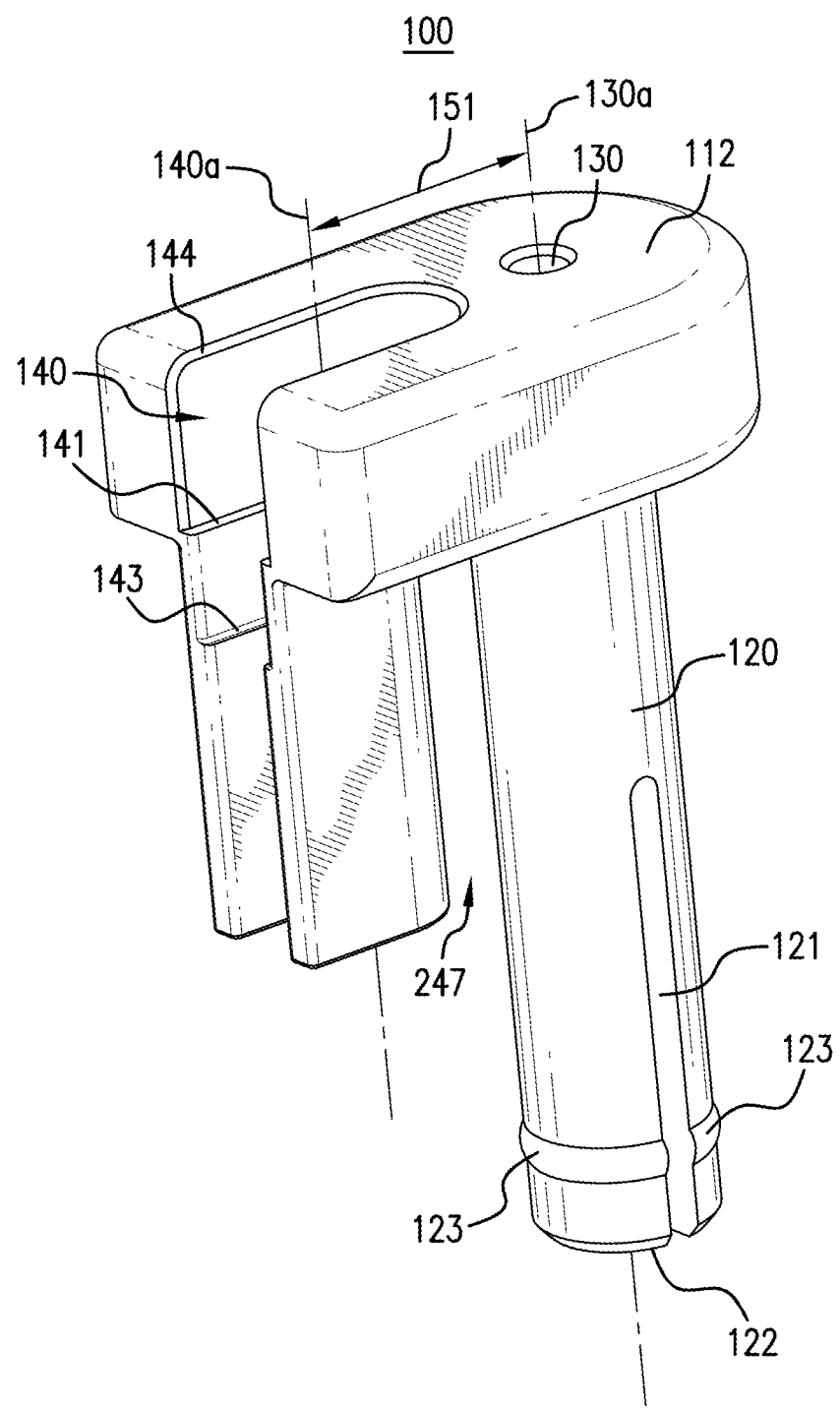
FIG. 1A is a perspective view of a parallel guide for joint fusion according to an embodiment.
Figure 1B:
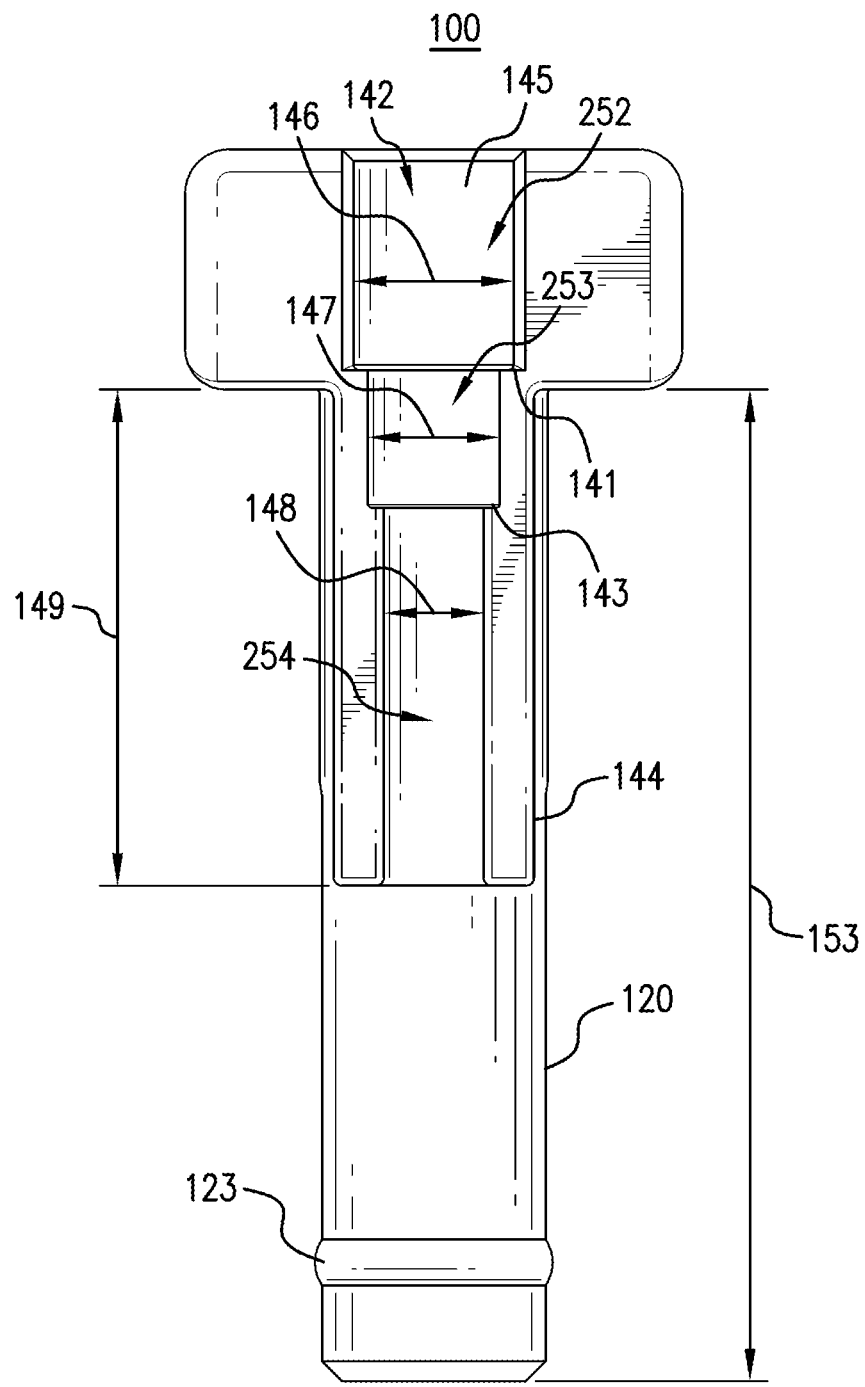
FIG. 1B is a rear view thereof.
Figure 1C:
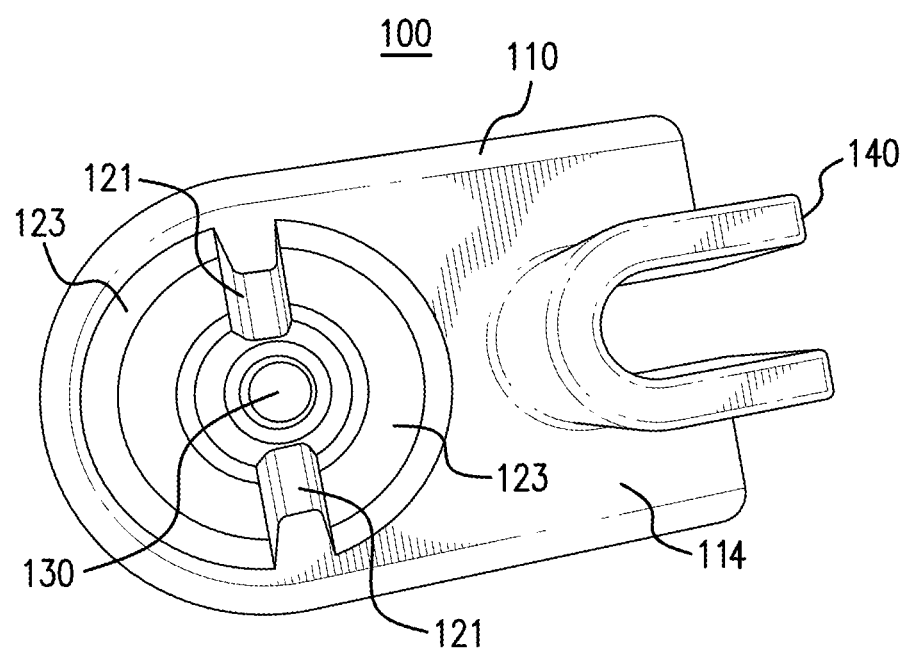
FIG. 1C is a distal view thereof.
Figure 1D:
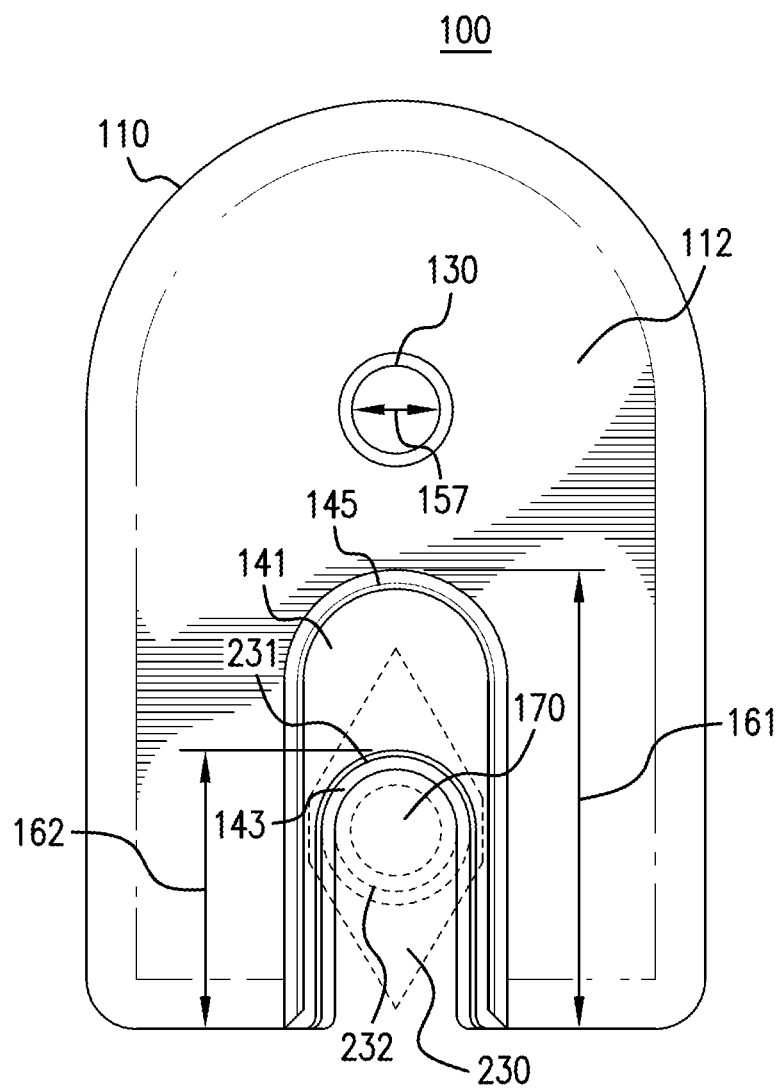
FIG. 1D is a proximal view thereof.
Figure 1E:
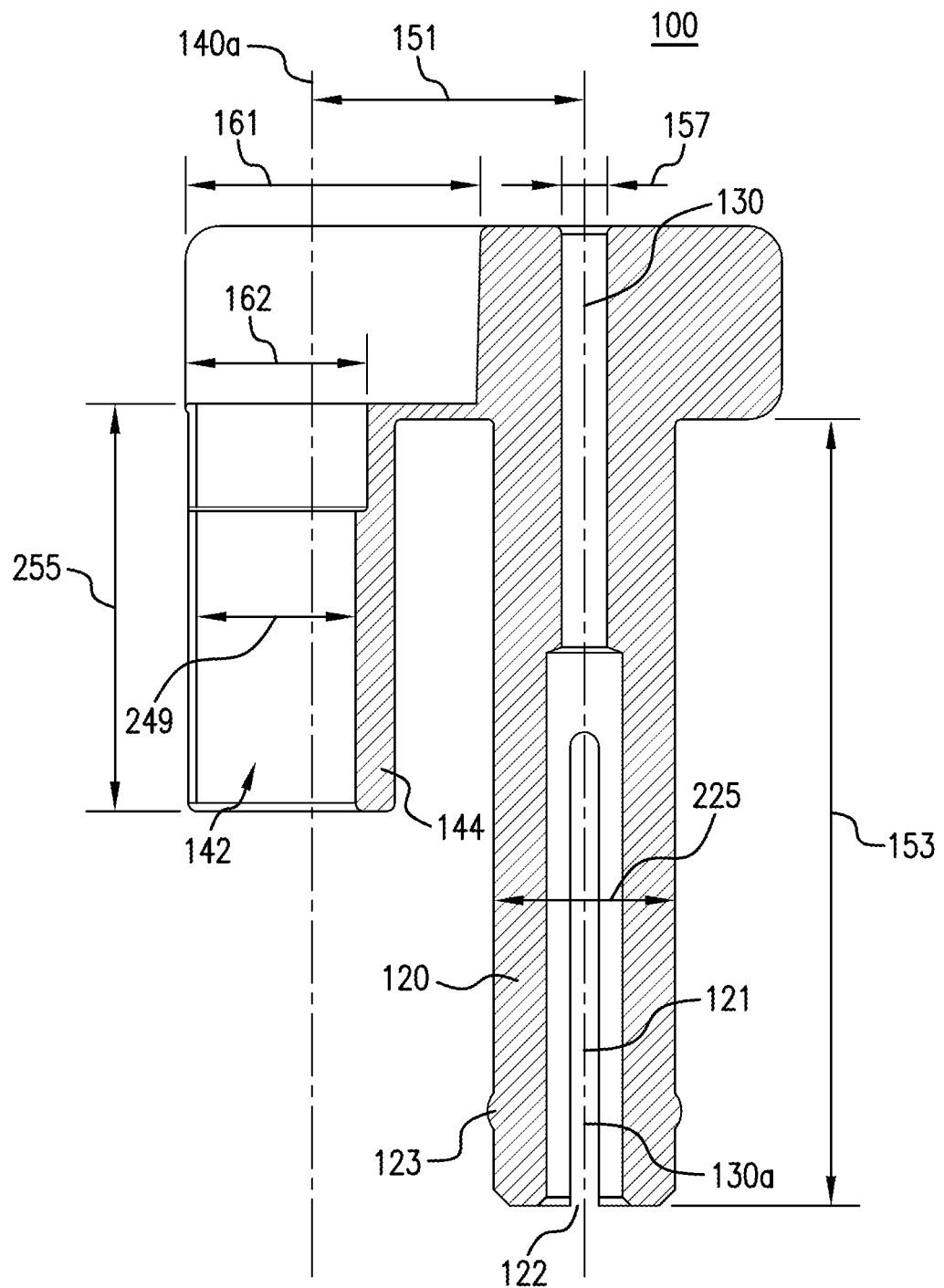
FIG. 1E is a sectional view thereof.

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are implicitly contemplated herein.

Techniques for joint fusion are described, including systems, apparatuses, and processes for fusing a joint. Some embodiments of systems and apparatuses for fusing a joint include a cage (i.e., a cannulated cage), a tissue protector assembly, a guide, a soft-tissue dilator, a cannulated drill bit (e.g., an adjustable cannulated drill bit that employs a stop collar), a driver, a parallel guide, and a plunger distance tool. As used herein, the term "cannulated" refers to having a cannula, or a hollow shaft. In some examples, the cage may be inserted or implanted into tissue (e.g., bone, cartilage, or other tissue in the joint). As used herein, the term "implant" or "implantation" refers to inserting or insertion into a part of a body. For example, a bone cage may be implanted into a joint (e.g., a sacroiliac joint). In some examples, the cage may have a cannula and radial fenestrations in which therapeutic materials may be packed. Such therapeutic materials may include osteogenic compounds (e.g., bone morphogenetic protein, or other osteogenic compounds that may ossify tissue in the joint), osteoconductive materials (e.g., demineralized bone, hydroxyapatite, or other material that promotes bone growth), antibiotics, steroids, contrast materials, or other materials that may beneficial to fusing the joint, treating inflammation or other conditions in the joint, or enabling the visualization of the area within and adjacent to an implanted bone cage. In some examples, the bone cage may be a screw or screw-type device having threads. In some examples, the screw may have one or more rows or groups of helical fenestrations along the wall (i.e., the shaft of the cage defining the cannula) of its shaft to allow the material packed inside the cannula of the cage to contact (e.g., touch, seep into, affect, communicate with, or otherwise physically contact) tissue adjacent to, surrounding, or even within, the cage. In some examples, various tools may be used to insert a cage into a location on a joint, and to prepare the location for the insertion procedure. Such tools may include, for example, an implantation assembly, which may comprise a tissue protector; a guide; a soft-tissue dilator; a cannulated drill bit; a driver; a parallel guide; a packing plunger, which may comprise a packing tube, a plunger and a loading port; a plunger distance tool; and other tools.

In some examples, a guide may be inserted first into a joint at a desired location. In some examples, a tissue protector assembly may be used, along with the guide, to guide the preparation (i.e., drilling) of a pilot hole as well as to guide insertion of a cannulated cage or other implant while forming a barrier between the preparation site and the surrounding tissue. In some examples, a cannulated drill bit may be used with the tissue protector and/or guide to drill the pilot hole. In some examples, a driver or screw driver may be used to insert the cage into the pilot hole. The term "driver" is used herein to refer to a tool configured to engage the head of a screw or similar device, typically via a tip of the driver, the tool being useful for rotating a screw or otherwise manipulating the screw to drive the screw or, in this case, cage into place in a joint. In some examples, a parallel spacer device may be used to space another guide in preparation for insertion of another cage. In some examples, a packing plunger assembly may be used to pack the cage with the above-mentioned materials. The packing plunger may be used to pack materials into the cage either or both pre- and post-insertion of the cage into the joint, and may be used with or without the tissue protector assembly.

FIGS. 1A-E are various views of a parallel guide 100 for joint fusion. Here, the parallel guide 100 includes a parallel spacer body 110 and an external positioning protrusion 120. The parallel spacer body 110 of this embodiment includes a primary or first guide aperture 130 suitable to receive one or more guiding elements 150 (shown in FIGS. 2-10) configured to guide the direction of one or more components including a drill bit. The guiding elements may include pins and wires (for example, Kirschner wires). The external positioning protrusion 120 extends from the parallel spacer body 110 and is suitable to engage with a tissue protector 180. The external positioning protrusion 120 is configured to have a diameter 157 suitable to enable the external positioning protrusion 120 to pass through the tissue protector 180. In some embodiments, the diameter of guide pins is approximately 1.5 and 6.5 mm. The diameter of Kirschner wires is approximately 0.9-1.5 mm. In the embodiment shown in FIGS. 1A-E, the external positioning protrusion 120 includes one or more deformation openings 121 and retention protrusions 123 configured to aid the external positioning protrusion 120 to enter the tissue protector and secure, through tension, to the inner surface of the tissue protector 180. In some examples, the parallel guide 100 may be configured to place another or a next guiding element 170 at a predetermined distance from a previously placed implant (i.e., a previously implanted screw or cage 200). Like-numbered and named elements in this view describe the same or substantially similar elements as in previous or subsequent views.

The parallel spacer body 110 includes a proximal surface 112 and a distal surface 114. While shown as opposing flat parallel surfaces, it is appreciated that these surfaces 112, 114 can have other suitable profiles, such as concave, convex and irregular surfaces. The parallel spacer body 110 of this embodiment has a sufficient depth to hold a guiding element 150 in a substantially constant angular position relative to the parallel guide 100. The parallel spacer body 110 has a suitable shape to keep each of the various apertures therethrough in a fixed relationship with each other.

The first guiding element aperture 130 extends through the parallel spacer body 110. The first guiding element aperture 330 has an axis 130a that orients the parallel guide 100 relative to the first guiding element 150 received through the aperture 130. The external positioning protrusion 120 includes a length 153 suitable for enabling the one or more guiding elements to be approximately aligned along axis 130a. In some embodiments, the length 153 is approximately 50-60 mm. The first guiding element aperture 130 includes an opening on the proximal end of the parallel guide 100. The opening extends into the parallel spacer body 110 from the proximal surface 112. In other examples, the opening may extend into the parallel spacer body 110 from a suitable surface on the proximal end of the parallel guide 100, such as a protrusion on the proximal end or like feature. The first guiding element aperture 130 includes an opening on the distal end of the parallel guide 100. The opening extends into the parallel spacer body 110 from a suitable surface on the distal end of the parallel guide 100. The aperture 130 extends from the proximal side opening to the distal side opening 122 on the distal surface on the external positioning protrusion 120. In other examples, the opening extends from a similar suitable feature, such as from the distal surface 114. The first guiding element 150 aperture 130 is defined by an interior surface that extends between the distal and proximal openings.

The parallel guide 100 includes a second guide aperture (i.e., second aperture functioning as an access needle guide port 140) configured to receive a subsequent access needle 160. The guide port 140 is a second aperture and is fixedly located relative to the first guiding element aperture 130, thereby defining a set distance and/or orientation between the guide port 140 and the aperture 130. In the embodiment of FIGS. 1A-E, the guide port 140 is configured to position the new access needle 160 (and accompanying guiding element 170) in relation to the previous guiding element 150 at fixed distance and orientation, which is preferably parallel. The guide port 140 is configured to enable an access needle 160 to be inserted into the guide port 140 and align the access needle 160 along an axis 140a that defines the orientation of the guiding element 170 of the access needle 160 relative to the parallel guide 100 as the guiding element 170 passes through the guide port 140. The guide port 140 includes an external positioning protrusion 144 that extends from the spacer body 110 in the direction of axis 140a. The external positioning protrusion 144 is configured to receive an access needle. The external positioning protrusion 120 and the external positioning protrusion 144 extend past the distal end 114 of the parallel spacer body 110. In the embodiment shown in FIGS. 1A-E, the external positioning protrusion 120 and the external positioning protrusion 144 are separated by a gap 247 configured to enable the external positioning protrusion 144 to be inserted into the tissue protector 180. When the external positioning protrusion 144 is inserted into the tissue protector 180, the external positioning protrusion 120 and the external positioning protrusion 144 extend past a proximal end 251 of the tissue protector 180.

The distance 151 between axis 130a and axis 140a is determinant upon the distance between implants. In the embodiment of FIGS. 1A-E, axis 130a and axis 140a are parallel. In the embodiment of FIGS. 1A-E, the distance 151 between axis 130a and axis 140a is approximately 20 mm. In some embodiments, the distance 151 is greater than 20 mm. In some embodiments, the distance 151 is less than 20 mm. In other examples, the distance between the axes is dependent upon the desired or required distance between implants.

The external positioning protrusion 144 is open from the proximal end of the parallel guide 100 laterally to the distal end and is configured to receive a stabilizing portion of a sheath of an access needle. The protrusion 150 aids in the alignment of access needle 160 along axis 140a. The guide port 140 includes a channel 142 configured to receive access needle 160. The external positioning protrusion 144 has a length 149 sufficient to enable the access needle to be approximately aligned with the access 130a through the channel 142. In some embodiments, length 149 is approximately 20-25 mm. In some embodiments, the length 149 is greater than 20 mm. In some embodiments, the length 149 is less than 20 mm. In the embodiment of FIGS. 1A-E, the channel 142 tapers from the proximal end toward the distal end (having a narrower width at the distal end than the proximal end), to increase contact between the new access needle 160 and the channel 142, increasing the alignment of the new access needle 160 along axis 140a. The length and dimensions of the tapered channel are configured to enable the access needle 160 to access the bone while inserted into the channel 142. In the embodiment of FIGS. 1A-E, the external positioning protrusion 144 tapers in a step-type fashion, which includes a series of narrowing steps 141, 143. The steps 141, 143 taper the channel 142 from a first width 146 to one or more decreasing widths 147, 148. In the embodiment shown in FIGS. 1A-E, the channel 142 includes three sections of varying widths, including a proximal section 252, having width 146, a middle section 253, having width 147, and a distal section 254, having width 148. The proximal section 252 may include a height to width ratio of approximately 2:1. In other embodiments, the height to width ratio of the proximal section 252 is approximately 3:1. In other embodiments, other suitable ratios may be used.

The middle section 253 may include a height to width ratio of approximately 1:1. In other embodiments, the height to width ratio of the middle section 253 is approximately 2:1 or approximately 3:1. In other embodiments, other suitable ratios may be used. The height to width ratio of the middle section 253 is configured to enable the access needle 160 to be aligned when the proximal section 231 of the sheath 175 is inserted into the middle section 253 of the channel 142.

The distal section 254 may include a height to width ratio of approximately 5:1. In other embodiments, the height to width ratio of the distal section 254 is approximately 4:1 or approximately 3:1. In other embodiments, other suitable ratios may be used.

The channel 142 has a length 255 from the proximal end of middle section 253 to the distal end of proximal section 254. In some embodiments, width 146 is approximately 5-10 mm, width 147 is approximately 5-10 mm, and width 148 is approximately 5 mm. In some embodiments, width 146 is less than 5 mm. In some embodiments, width 146 is greater than 10 mm. In some embodiments, width 147 is less than 5 mm. In some embodiments, width 147 is greater than 10 mm. In some embodiments, width 148 is less than 5 mm. In some embodiments, width 148 is greater than 5 mm. In other embodiments, the tapering may conform to other shapes such as, for example, gradual linear tapering or curved tapering. In yet other embodiments, the width and/or diameter of the external positioning protrusion 144 is consistent from the proximal end to the distal end. In the embodiments of FIGS. 1A-E, the widths of the steps 141, 143 range from 5-8 mm. In other embodiments, the widths of the steps 141, 143 include other dimensions. The width 146 enables a handle connection section of the access needle to be inserted into the channel 142 above the first step 141. The steps 141, 143 cause the diameter of the channel 142 to narrow, preventing the handle connection section from passing through the channel, limiting how far the access needle can pass through the channel 142 and, therefore, how far the access needle can be inserted into the bone. In the embodiments of FIGS. 1A-1E, the channel 142 includes a plurality of depths 161, 162, 249. In some embodiments, depth 161 is approximately 15-20 mm, depth 162 is approximately 10-15 mm, and depth 249 is approximately 10-15 mm. In some embodiments, depth 161 is less than 15 mm. In some embodiments, depth 161 is greater than 20 mm. In some embodiments, depth 162 is less than 10 mm. In some embodiments, depth 162 is greater than 15 mm. In some embodiments, depth 249 is less than 10 mm. In some embodiments, depth 249 is greater than 15 mm. The decrease in depth further prevents the handle connection section from passing through the channel 142.

In the embodiment of FIGS. 1A-E, the channel 142 extends through the aperture 140 from the proximal end 112 of the parallel spacer body 110 to the distal end of the external positioning protrusion 144 faces away from the first guiding element aperture 130. In the embodiment of FIGS. 1A-E, the aperture 140 is open from the proximal end 112 of the parallel spacer body 110 to the distal end of the external positioning protrusion 144 in a direction radial to axis 130*a*. In various embodiments, the aperture 140 is open from the proximal end 112 of the parallel spacer body 110 to the distal end of the external positioning protrusion 144 in a direction radial to axis 140*a*.

The external channel 142 enables an access needle 160 to be inserted and/or removed from the channel 142 radially with respect to the axis 140*a* by tilting the tissue protector 180 with the parallel guide 100 still mounted in the tissue protector with the guiding element 150 or other protrusion received in the bone 237. In other embodiments, the channel 142 faces a different direction in relation to the first guiding element aperture 130, and in some embodiments the different direction is also suitable for radial insertion or removal of the access needle into or from the channel 142 of the second aperture 140, such as by tilting the tissue protector and parallel guide.

In the embodiment of FIGS. 1A-E, the inner surface 145 of the channel 142 is rounded. The inner surface 145 defines the second aperture 140. The rounded inner surface 145 are configured to enable a close fit of a portion of an exterior of one or more portions of the access needle within the channel 142, enabling rotational movement of the access needle 160 while the access needle 160 is positioned within the channel 142, which aids in the insertion of the access needle 160 into the bone. In other embodiments, the inner surface of the channel 142 may conform to other shapes, such as matching the shape of an intended, corresponding access needle. For example, in other embodiments, the inner surface of the channel 142 may be flat and/or may include one or more corners.

The external positioning protrusion 120 is suitably connected to the parallel spacer body 110 so as to constrain and/or position the tissue protector 180 relative to the parallel spacer body 110. For example, the external positioning protrusion 120 may be of unitary construction with the parallel spacer body 110. The external protrusion has an outer diameter suitable to be received into the tissue protector 180 and a length configured to further stabilize and more precisely align the access needle 160. In the embodiments of FIGS. 1A-E, the external protrusion has an inner diameter (e.g. along the aperture 130 which could be stepped in diameters to accommodate both the guiding element and the tissue protector) suitable to receive the tissue protector 180.

Figure 2:
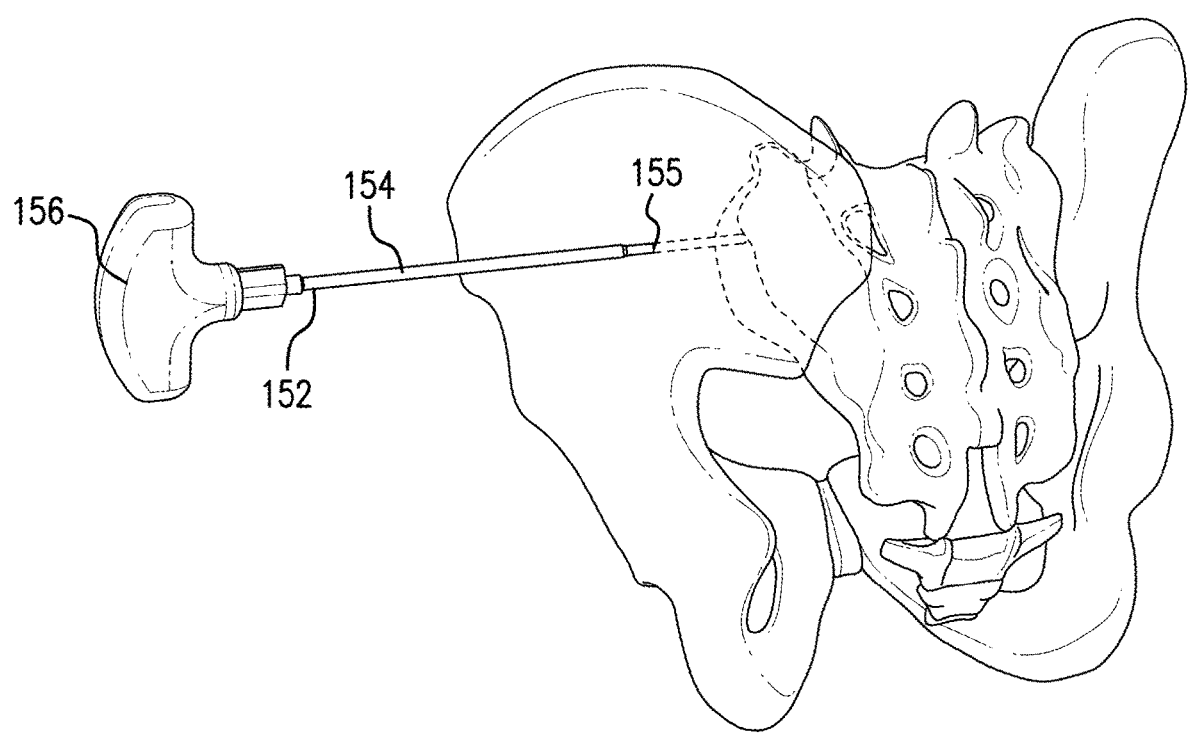
FIG. 2 is a perspective view of an access needle being inserted into a bone, in accordance with an embodiment.
Figure 3:
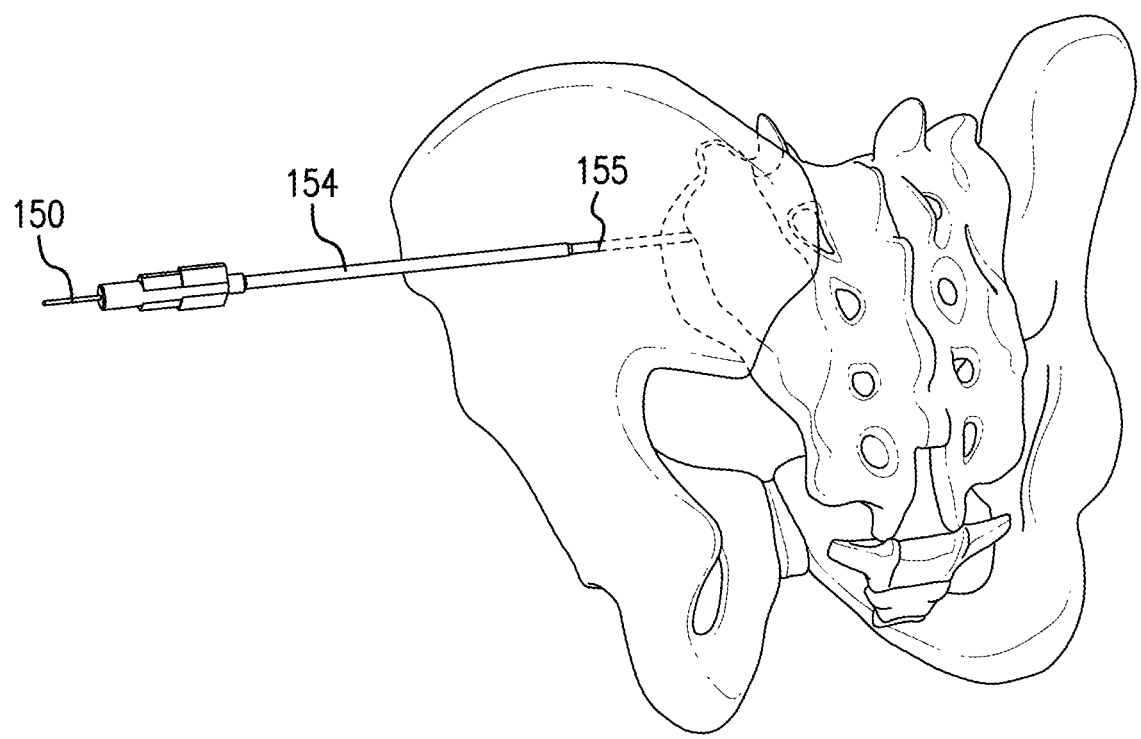
FIG. 3 is a perspective view of a guiding element of the access needle of FIG. 2 inserted into a bone after the handle has been removed.

As illustrated in FIGS. 2-10, the procedure for placing a series of implants into bone are illustratively depicted. As shown in FIG. 2, a first access needle 152, having a sheath 154, handle 156, and guiding element 150, is inserted into bone, at 155. According to various embodiments, the guiding element 150 protrudes from the sheath 154 on the end opposite the handle 156 and extends through the sheath 154 and into the handle portion 156. The handle portion 156 is removable, exposing the guiding element 150, which is inserted into the bone, as shown in FIG. 3. Subsequent to the handle portion 156 being removed, the sheath 154 is removed, leaving the guiding element 150 positioned within the bone.

Figure 4:
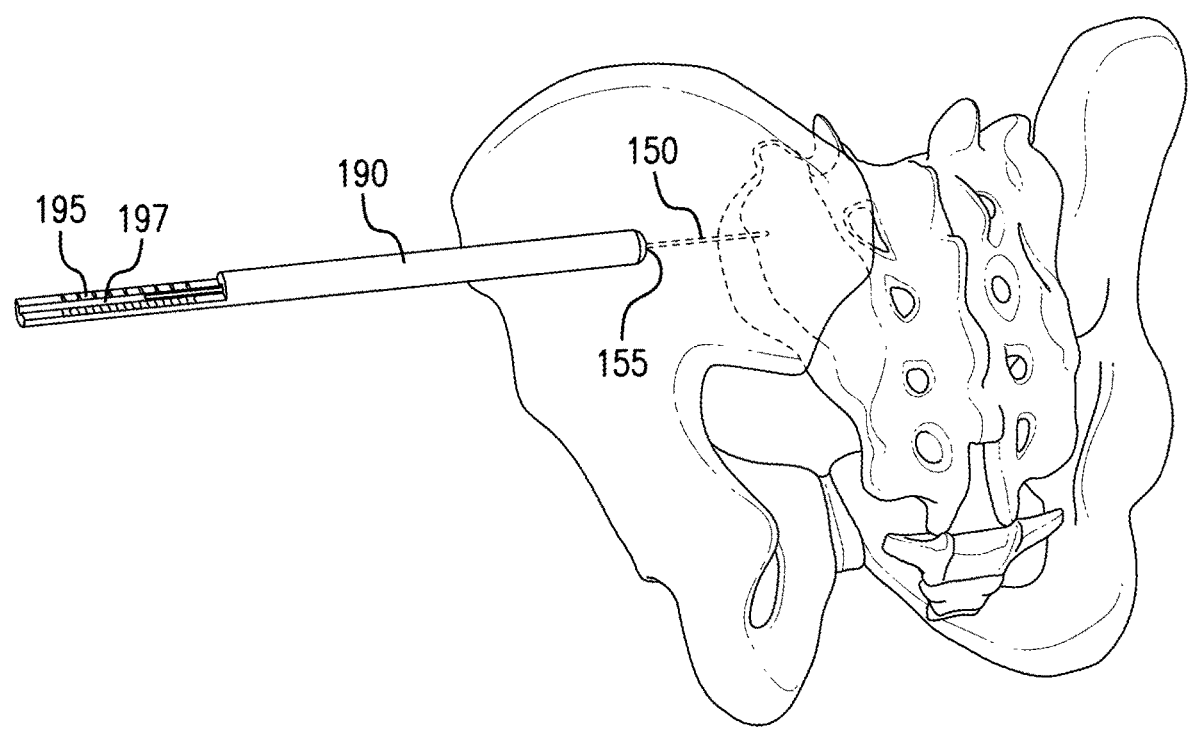
FIG. 4 is a perspective view of a soft-tissue dilator positioned over the guiding element of FIG. 3.
Figure 5:
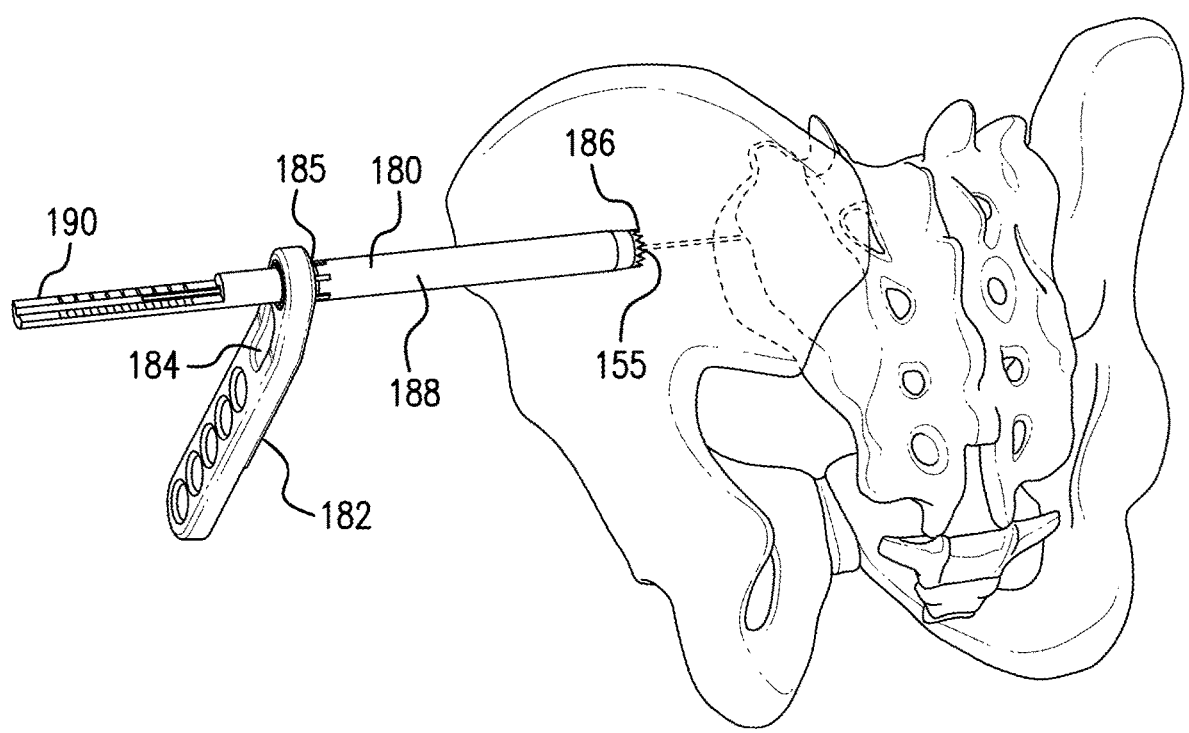
FIG. 5 is a perspective view of a tissue protector positioned over the dilator of FIG. 4.

A soft-tissue dilator 190 is placed over the exposed guiding element 150, as shown in FIG. 4. The soft-tissue dilator 190 is configured to determine the depth of a guide 150 to be inserted into the bone. In the embodiment of FIGS. 4 and 5, the soft-tissue dilator 190 includes depth markings 195 and a channel 197 through which the guiding element 150 can pass. The channel 197 is formed along an exposed wall of the depth gage 190. The channel 197 transitions into an enclosed channel through a lower body portion of the soft-tissue dilator 190. The contact surface is located on the distal end of the lower body portion and is suitable to contact the bone. The guiding element 150 can then be slid into the soft-tissue dilator 190 to the desired depth as measured on the depth markings 195. The soft-tissue dilator 190 is configured to determine the depth in which the guiding element 150 is inserted into a bone and/or joint. The depth markings 195 can measure the depth in which the guiding element 150 is driven into the bone. Typically, the depth markings 195 range from around 25-65 mm depths, but in other embodiments, different range markings can be provided. The number in depth markings 195 that corresponds to the location of the end of guiding element 150 indicates the depth of the guide 150. In other examples, the depth markings can indicate a different depth that may correspond and be calibrated to the depth of the guiding element 150 (e.g., the depth markings may indicate a desired drilling depth for a pilot hole, a depth of a cage to be implanted, and/or other depth that is associated with the depth of the guiding element 150, and may thus be measured against the depth of guiding element 150). Other embodiments include a soft-tissue dilator that does not have depth markings, and in some embodiments, the process can be practiced without using the soft-tissue dilator, depending on the location of the surgery.

In FIG. 5, a tissue protector assembly 180 is shown placed over the guiding element 150 and the soft-tissue dilator 190. The tissue protector 180, in this example, includes a tissue protector sleeve 188, handle 182, tissue protector head 185, tissue protector tip 186 and the depth gage 190 (functioning as a guide sleeve for a pin or wire), but other types of tissue protectors can alternatively be used. The sleeve 188 of tissue protector assembly 188 has a hollow shaft having a close fit to one or more of the soft-tissue dilator 190, the cage or screw 200, and/or a drill 210. In some examples, the outer diameter of sleeve (e.g., soft-tissue dilator 190) shaft is shaped to fit inside the cannula of the tissue protector 180, which has an internal diameter that may be configured to accommodate tools and implants (e.g., cages 200, and the like) having a larger diameter than a guide. For example, the diameter of tissue protector's cannula may correspond to (i.e., be sized to fit) the head or outer diameter on an implant (e.g., cages 100). In some examples, the internal surface of tissue protector 180 may be configured to guide an implant (e.g., cage 200) inserted into the tissue protector 180 from the tissue protector head 185 and through to tissue protector tip 186.

In some examples, the tissue protector tip 186 includes spikes, teeth, wedges, and/or other structures, to engage a bone. In the embodiment shown in FIG. 5, the tissue protector tip has relatively blunt teeth or other feature that are not embedded into the bone, but merely increases friction such that the tissue protector tip 186 does not slip on the exterior of the bone. Some embodiment has a tissue protector with a smooth, non-serrated distal end.

Figure 6:
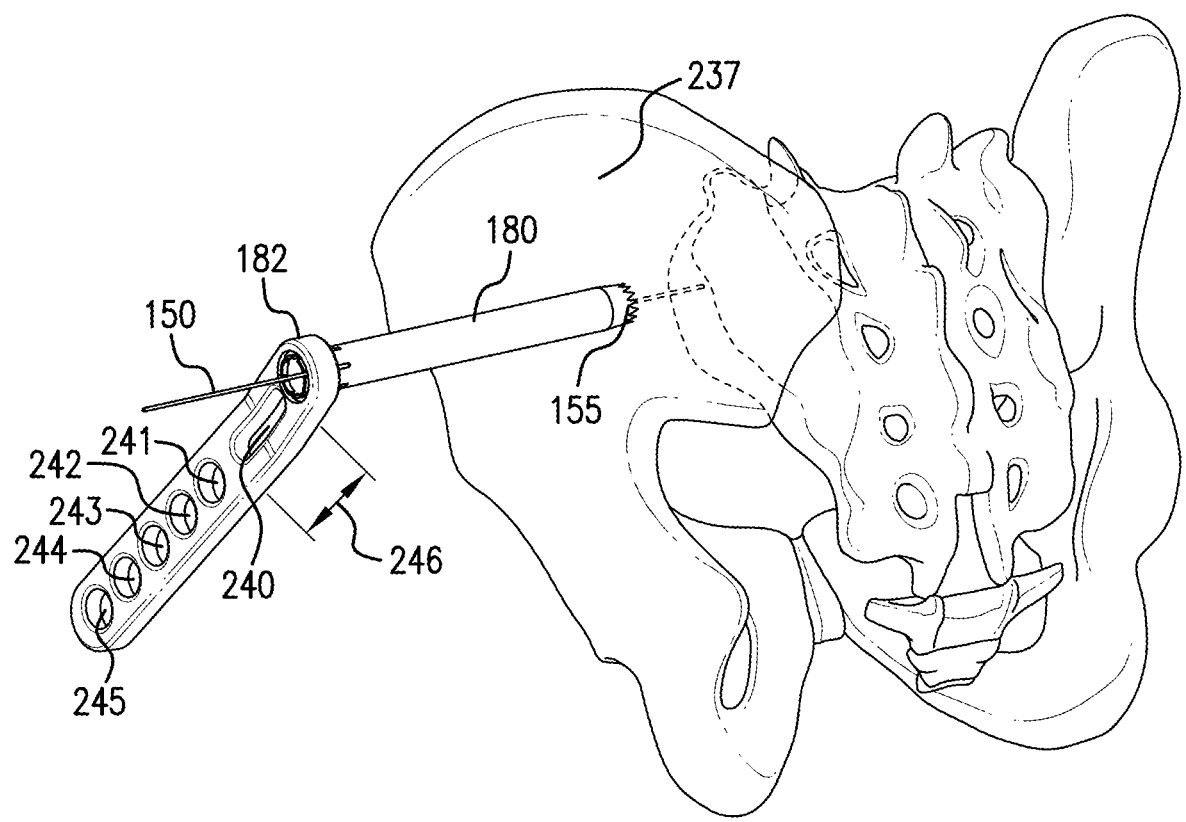
FIG. 6 is a perspective view of the assembly of FIG. 5 with the dilator removed.
Figure 7:
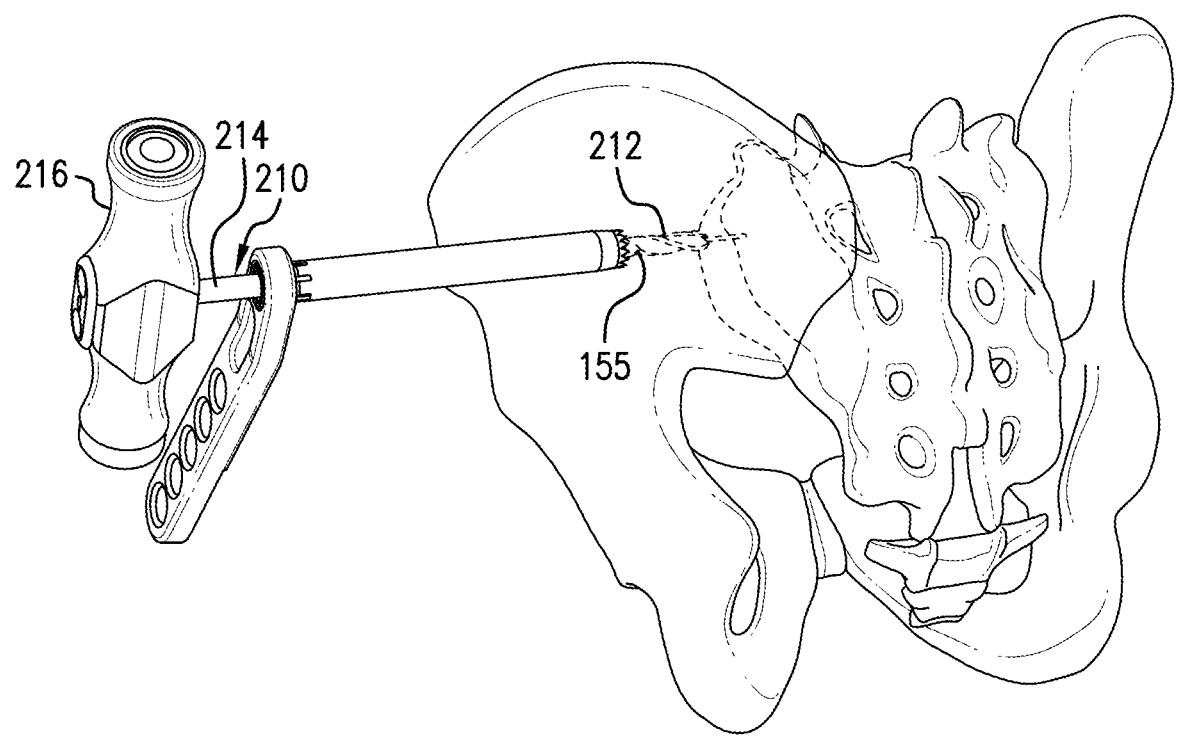
FIG. 7 is a perspective view of a cannulated drill bit drilling into the bone over the guiding element and within the tissue protector of FIG. 6.

The soft-tissue dilator 190 is removed from the tissue protector 180, as shown in FIG. 6, and replaced with a cannulated drill bit 210, as shown in FIG. 7, for drilling a pilot hole for insertion of a cage for joint fusion 200. Here, the cannulated drill bit 210 may include a cutting tip 212, body 214, and shank. As used herein, "drill bit" refers to a cutting tool configured to create substantially cylindrical holes, and "shank" refers to an end of the drill bit, usually the end opposite the cutting tip, configured to be grasped by a chuck of a drill, handle 216 or other torque applying device. In some examples, the cannulated drill bit 210 is configured to drill a pilot hole to a predetermined depth. For example, cutting tip 212 is configured to cut cylindrical holes into a bone and/or joint when torque and axial force is applied to rotate cutting tip 212 (i.e., by a drill). In other examples, the cannulated drill bit 210 is adjustable, and thereby configured to drill a range of depths using depth markings. In the embodiment of FIG. 7, the outside diameter of the cannulated drill bit 210 is configured to fit within a tissue protector (e.g., tissue protector 180). In other examples, the outside diameter is significantly smaller than the tissue protector 180, such that the tissue protector does not provide significant support to the drill bit 210 or function as the primary locating tool for the drill bit 210. In other examples, the tissue protector 180 functions as the drill guide, providing significant support and locating functionality to the drill bit 210 by having an inner diameter that is substantially the same size as the outer diameter of the drill bit 210, the variance in sizes being sufficient to allow the drill bit 210 to slide and rotate within the tissue protector 180.

In some examples, a desired drilling depth (i.e., depth of a pilot hole) is the same or similar to the depth of a guide that has been inserted into a bone and/or joint. In other examples, the desired drilling depth may be offset (i.e., less deep) by a predetermined amount (e.g., a few millimeters or other offset amount). For example, if a guide has been inserted 40 mm deep into the sacroiliac joint, a corresponding desired drilling depth for the pilot hole may be 40 mm, or it may be 40 mm minus the predetermined offset may be selected (i.e., if the predetermined offset is 3 mm, then the desired drilling depth in this example would be 37 mm).

The cannulated drill bit 210 includes cannula. In some examples, the cannula is sized to fit over a guiding element (e.g., guiding element 150). A driver handle 216 receives the shank, allowing a user to apply a torque to the drill bit 210. The drill bit 210 is slid down over the guiding element 150, thereby accurately locating the drill bit 210 based on the insertion location of the guiding element 150 into the bone. The tissue protector 180, particularly the sleeve 188 thereof protects the tissue surrounding the drilling site from being damaged by the drilling action. The drill forms hole through one or more bones (e.g., ilium and/or Sacrum).

Figure 8:
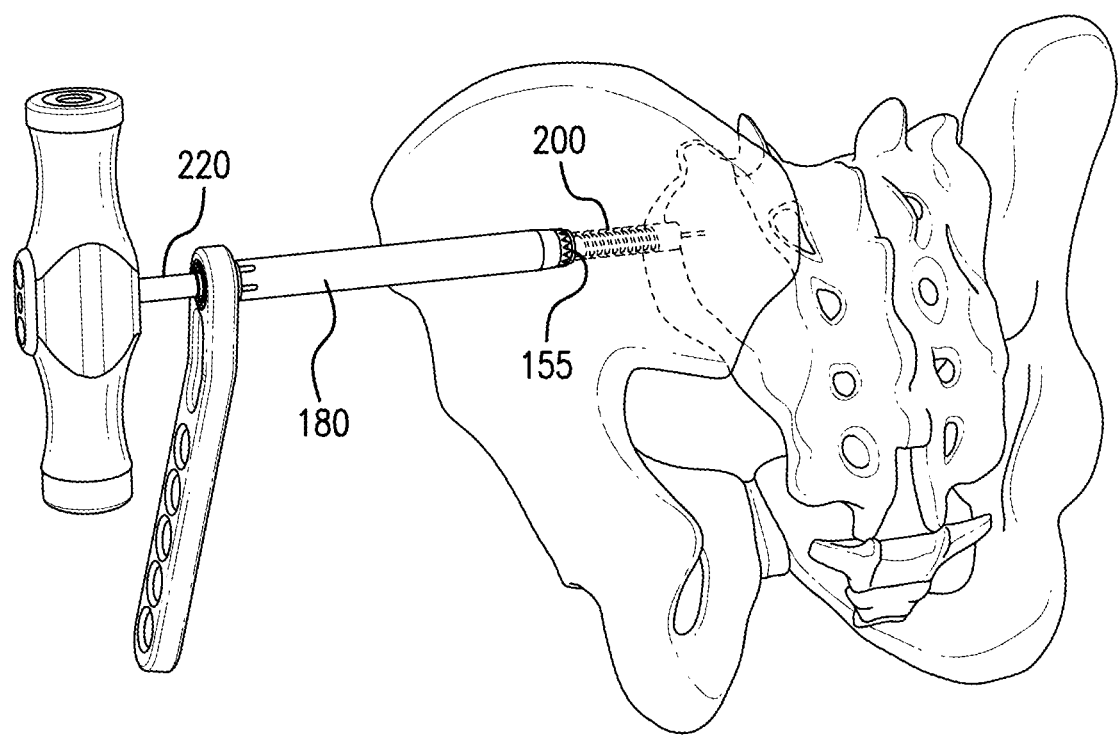
FIG. 8 is a perspective view of a driver driving an implant into a bone over the guiding element and within the tissue protector of FIG. 7.

The cannulated drill 210 is replaced with a driver 220, as shown in FIG. 8, for inserting an implant 200 into the joint for fusion. As used herein, a cage 200 is provided as an example, but it is noted that bone screws for joint fusion can also be used. The cage 200 includes head, tip, one or more groups of helical fenestrations (e.g., fenestration groups), threads, and tapered end. In some examples, cage 200 is fabricated, manufactured, or otherwise formed, using various types of medical grade material, including stainless steel, plastic, composite materials, or alloys (e.g., Ti-6Al-4V ELI, another medical grade titanium alloy, or other medical grade alloy) that may be corrosion resistant and biocompatible (i.e., not having a toxic or injurious effect on tissue into which it is implanted). In some examples, threads include a helical ridge wrapped around an outer surface of cage 200's shaft. In some examples, cage 200 is cannulated, having a cannulated opening formed by a hollow shaft that extends from head to tip. Cage 200 may vary in length (e.g., ranging from approximately 25 mm to 50 mm, or longer or shorter) to accommodate size and geometric variance in a joint. Other dimensions of cage 200, including major and minor diameters of threads, also may vary to accommodate size and geometric variance in a joint. In some examples, an outer surface of cage 200's shaft tapers from head to tapered end, and thus threads also may taper (i.e., be a tapered thread) from head to tapered end (e.g., having a range of major and minor diameters from head to tapered end). In some examples, the tapering of threads, as well as tapered end, aids in guiding the cage through a pilot hole. In other examples, head and threads are sized to fit within a tool or instrument, for example, a tissue protector 180, as described herein.

In some examples, cage 200's hollow shaft, or cannula, is accessed (i.e., for packing material into) through an opening in head. In some examples, head may have a flat or partially flat surface (e.g., pan-shaped with rounded edge, unevenly flat, or other partly flat surface). In other examples, head has a different shape (e.g., dome, button, round, truss, mushroom, countersunk, oval, raised, bugle, cheese, fillister, flanged, or other cage head shape). In some examples, the opening in head has a receiving apparatus for a torque applying tool, such as driver. The driver may be a flat head, Phillip's head, square head, hexagonal, head or other shape suitable to receive a tool and apply torque therefrom. In one example, the torque applying tool may be a driver having a TORX® or TORX®-like shape (i.e., six-point or six-lobed shape) configured to receive the tip of a TORX® or TORX®-like screwdriver (e.g., driver 220). For example, cage 200 may include head grooves which may start at head and extend linearly into the cannula of cage 200 to receive complementary lobes on the end of a screwdriver. For a TORX® or TORX®-like opening there may be six (6) total head grooves, including, for example, head grooves, to receive the complementary lobes on the tip of a TORX® or TORX®-like driver. In some examples, the opening in head may be contiguous with, and form a proximal end of, cage 200's cannula. For example, the opening may provide access to the cannula, for example, to pack material into the cage. The opening may also include a chamfer providing a lead-in for a tool into the head grooves.

As described herein, therapeutic materials include osteogenic compounds (e.g., bone morphogenetic protein, or other osteogenic compounds that may ossify tissue), osteoconductive materials (e.g., demineralized bone, hydroxyapatite, or other material that promotes bone growth), antibiotics, steroids, contrast materials, or other materials that may be beneficial to fusing the joint, treating inflammation or other conditions in the joint, or enabling the visualization of the area within and adjacent to the cage. For example, an osteogenic compound, such as bone morphogenetic protein or other compounds, may be packed into cage 100's cannula such that when cage 100 is inserted into a joint or traverses through a joint (e.g., a sacroiliac joint), the osteogenic compound, for example through fenestrations, may come into contact with tissue in the joint adjacent to or surrounding cage, and ossify the tissue to fuse the joint across and through the cage. In some examples, the osteogenic compound may enter the joint and may fill the joint, partially or entirely. In other examples, an osteoconductive material, such as demineralized bone or hydroxyapatite or other materials may be packed into cage's cannula. When cage is inserted into a joint (e.g., the joint between ilium I and sacrum S), the osteoconductive material may come into contact with tissue in the joint adjacent to or surrounding cage, for example through fenestrations, and promote bone growth into the cage and the joint to fuse the joint across and through the cage. In still other examples, a substance for treating sacroiliitis, such as steroids or antibiotics or other substances, may be packed into cage's cannula such that when cage is inserted into the joint, the substance may come into contact with tissue in the joint adjacent to or surrounding cage, for example through fenestrations, and treat the inflamed joint tissue. In yet other examples, a contrast material may be packed into cage's cannula such that, when cage is inserted into the joint, the contrast material within cage, and in some examples absorbed by tissue adjacent to or surrounding cage, may be viewed using visualization techniques (e.g., x-ray, fluoroscope, ultrasound, or other visualization technique). In still other examples, different materials may be packed into cage for different purposes. In yet other examples, the above-described materials may also come into contact with tissue adjacent to, or surrounding, cage through an opening at tip. As described herein, cage may be packed with material prior to being inserted into the joint, and may also be packed after insertion into the joint. Also as described herein, such materials may be packed into cage using a packing plunger.

In some examples, fenestrations may provide therapeutic openings in cage's shaft to enable material packed inside cage to come into contact with surrounding or adjacent tissue (e.g., bone, cartilage, or other tissue in the joint) when cage is implanted. Additionally or alternatively, in various examples, the fenestrations may be shaped to provide additional cutting edges or edges suitable to clean threads formed by the tip. In various examples, fenestrations are substantially circular. In other examples, the fenestrations are oblong (e.g., substantially oval, substantially elliptical, or other suitable shapes). In other examples, fenestrations are shaped differently (e.g., rectangular, rounded rectangular, squared, triangular, or other suitable shapes). In accordance with various embodiments and discussed herein.

Figure 9:
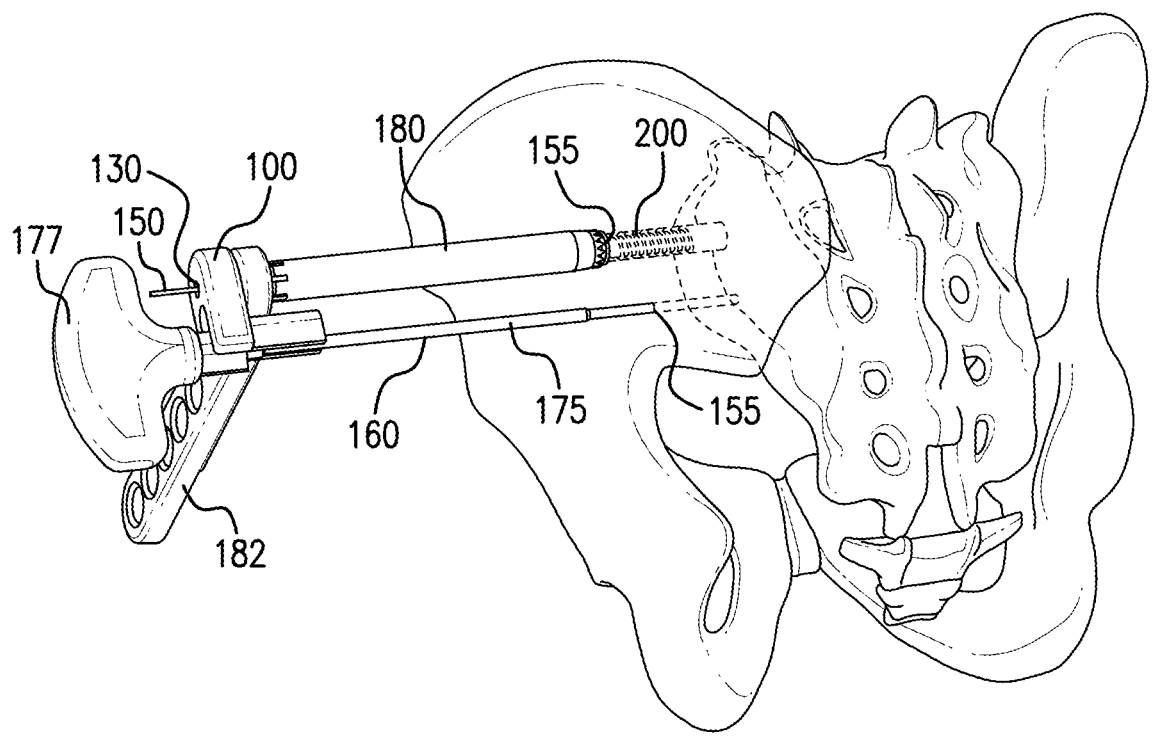
FIG. 9 is a perspective view of the parallel guide of FIGS. 1A-E guiding a second access needle into a bone.
Figure 11:
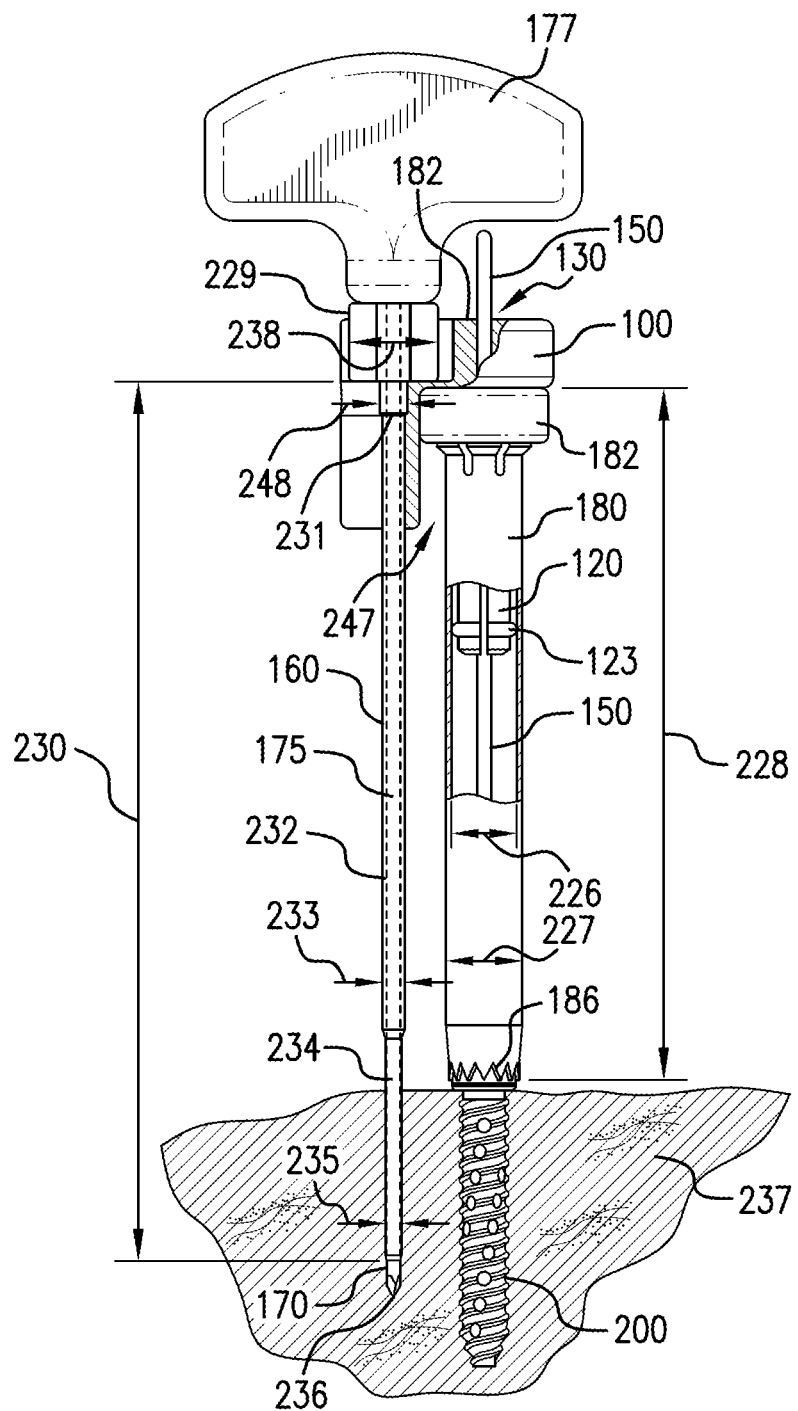
FIG. 11 is a cutaway view of the assembly of FIG. 9.

FIG. 9 illustrates a view of an exemplary parallel guide 100 for placement of a new access needle 160 as placed on a drill guide. A partially sectional view of the components as shown in FIG. 9 is illustrated in FIG. 11. As shown, external positioning protrusion 120 may fit into tissue protector 180, which has a length 228, an outer diameter 227, an inner diameter 226 configured to receive the external positioning protrusion 120, which has a diameter 225. The inner diameter 226 of the tissue protector 180 is configured to enable the external positioning protrusion 120 to fit snugly within the tissue protector 180. In some embodiments, the diameter 225 of the external positioning protrusion 120 is approximately 10-20 mm. In some embodiments, the inner diameter 226 of tissue protector 180 produces a snug fit between the inner surface of the tissue protector 180 and the outer surface of the external positioning protrusion 120. In the embodiment shown in FIG. 11, protrusion 123 maintains contact with the inner surface of the tissue protector 180. The length 228 of the tissue protector 180 is sufficient to fully encapsulate the external positioning protrusion 120. In some embodiments, the length 228 of the tissue protector 180 is approximately 120-130 mm. In some embodiments, the length 228 is less than 120 mm. In some embodiments, the length 228 is greater than 130 mm. In the embodiments of FIGS. 9 and 11, part of the parallel guide 100 rests against the tissue protector 180.

The access needle 160 is configured to enable insertion of a guiding element 170 within bone 237. In various embodiments, the access needle may be a commercially available access needle such as, for example, the Jamshidi™ Needle, the Medtronic PAK Needle, the Preston™ Bone Access Needle, the Laurane® Vertebroplasty/Cementoplasty Introducer, or other suitable access needle.

The access needle 160 may include a guiding element 170, sheath 175, handle connection section 229, and handle 177. The handle connection section 229 is configured to secure the handle 177 to the access needle 160 and is configured to enable introduction and removal of the handle 177 from the access needle 160 (to enable access to the guiding element 170 within the access needle 160). The handle connection section 229 may be rounded and/or include a plurality of sides. In the embodiment of FIGS. 9 and 11, handle connection section 229 has a diamond-shaped cross-section. In some embodiments, the handle connection section 229 includes one or more shapes such as, for example, rounded or circular shapes, rectangular shapes, triangular shapes, etc. In some embodiments, a width of the protruding section is approximately matching to a width of the channel 142. The handle connection section 229 has a width 238 of sufficient size to prevent the handle connection section 229 from passing through proximal section 252 of the channel 142. In some embodiments, the handle connection section 229 has a width 238 of approximately 10-20 mm. In other embodiments, the diameter 238 of the handle connection section 229 may be less than 10 mm or greater than 20 mm.

In the embodiment shown in FIG. 11, the access needle 160 includes a sheath 175 having a length 230 and a proximal section 231, a middle section 232, and a distal section 234. The proximal section 231 has a width 248. In some embodiments, the width is approximately 5-15 mm. In some embodiments, width 248 is less than 5 mm. In some embodiments, width 248 is greater than 15 mm. In some embodiments, the proximal section 231 of the sheath 175 functions as a guiding section. The width 248 of the proximal section 231 is configured to be approximately the same as the width 147 of the middle section 253 of the channel 142. In various embodiments, the proximal section 231 of the sheath 175 is sized to enable insertion into and/or rotation within the middle section 253 of the channel 142.

The middle section 232 of the sheath 175 has a diameter 233 and is configured to remain external to the bone 237. The middle section 232 is configured to be inserted within the distal section 254 of the channel 142. In some embodiments, the proximal section 232 has a diameter 233 of approximately 1-5 mm. In other embodiments, the diameter may be greater than 5 mm. The proximal section 234 has a diameter 235 and is configured to be partially or entirely inserted into the bone 237. The guiding element 170 extends from the proximal section 234. In the embodiment of FIG.

11, the guiding element 170 ends with an insertion point 236. The proximal section 234 is inserted into the bone 237 by threading, hammer, pressing or similar method. In some embodiments, the diameter 235 of the distal section 234 is approximately 1-2 mm. In the embodiment shown in FIG. 11, the access needle 160 tapers between sections 231, 232, and 234. The taper may be linear, curved, gradual, immediate, or other suitable form of taper.

Figure 10:
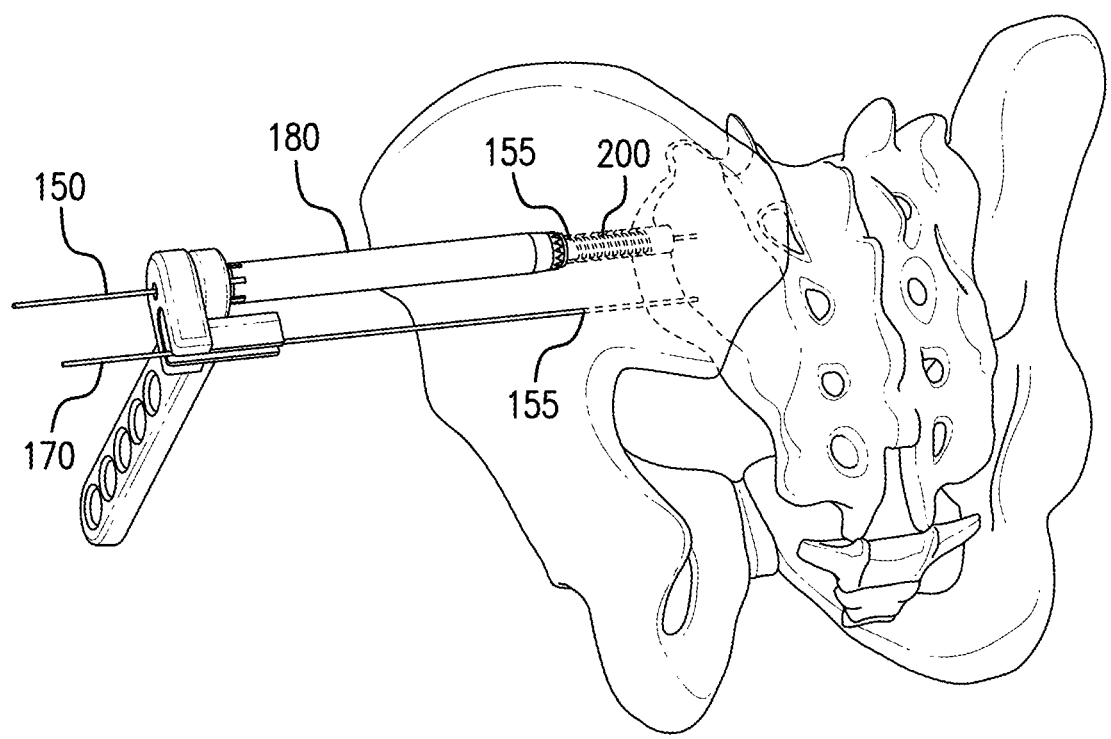
FIG. 10 is a perspective view of a first guiding element and a second guiding element inserted into a bone and spaced via the parallel guide of FIG. 10.

In some examples, the tissue protector 180 is slid over the soft-tissue dilator 190 to locate the tissue protector 180. In other examples, the tissue protector 180 is located first and then the guide 150 and soft-tissue dilator 190 are inserted into the tissue protector 180. In the embodiment of FIG. 9, the handle portion 182 of the tissue protector 180 includes a guiding hole 240 configured to be used as an access needle guide separate and apart from the parallel guide 100. The guiding hole 240 includes an inner surface 250 at a distance 246 from guiding element 150. In some embodiments, the distance 246 is approximately 5 mm. In some embodiments, the distance is less than 5 mm. In some embodiments, the distance 246 is greater than 5 mm. In the embodiment of FIG. 6, the handle portion 182 of the tissue protector 180 includes one or more additional holes 241, 242, 243, 244, 245, each having a center axis at a set distance from the guiding element 150 and which can be used to guide an access needle into bone at a set distance from the guiding element 150, causing the handle portion 182 of the tissue protector 180 to act as a second guiding element spacer. The external positioning protrusion 120 fits over the first guiding element 150 via aperture 130. The parallel guide 100 enables the new wire guide 170 to be placed a set distance from the primary wire guide 150, as shown in FIG. 10.

Although the foregoing examples have been described in some detail for purposes of clarity of understanding, the invention is not limited to the details provided. There are many alternative ways of implementing the invention.

What is claimed is:

1. A parallel spacer for parallel spacing of a plurality of guiding elements during surgery, comprising:
    a first guide portion that defines a first guide aperture extending through the first guide portion between an opening in a proximal surface and an opening in a distal surface of the first guide portion, the first guide aperture being sized to receive an elongated guiding element and hold a first orientation of the first guide portion with respect to the guiding element; and
    a second guide portion that defines a second guide aperture extending through the second guide portion between an opening in a proximal surface and an opening in a distal surface of the second guide portion, the second guide aperture being sized to receive and hold an access needle parallel to the first orientation, the second guide aperture defining an open side connecting the openings in the proximal and distal surfaces of the second guide portion and configured and dimensioned to receive or extract therefrom the access needle.

2. The parallel spacer of claim 1, wherein the first and second guide apertures are parallel to each other.

3. The parallel spacer of claim 2, wherein the second guide aperture is configured as an open channel having the open side, which open side is open in a direction radial to an axis of the channel that runs between the openings in the proximal and distal surfaces of the second guide portion, which open side enables the access needle to be extracted radially from the channel through the open side.

4. The parallel spacer of claim 3, wherein the channel includes a rounded inner surface configured to facilitate rotational movement of the access needle within the channel.

5. A system for parallel spacing a plurality of guiding elements during surgery, comprising:
    the parallel spacer of claim 3; and
    the access needle, which is configured and dimensioned to be held by the channel parallel to the first guide aperture and such that the access needle is extracted from the open side of the channel.

6. The parallel spacer of claim 1, wherein the second guide aperture is disposed to hold the access needle parallel to, and at a fixed distance from, the guiding element received in the first guide aperture.

7. The parallel spacer of claim 1, wherein the second guide aperture narrows toward a distal end of the second guide aperture.

8. The parallel spacer of claim 1, wherein the first guide portion includes a first protrusion that includes the distal surface of the first guide portion and that extends distally past another distally facing surface of the parallel spacer, the first guide aperture extending through the first protrusion.

9. The parallel spacer of claim 8, wherein the second guide portion includes a second protrusion that includes the distal surface of the second guide portion and that extends distally past the another distally facing surface of the parallel spacer, thereby defining a gap between the first and second protrusions, the second guide aperture extending through the second protrusion, thereby lengthening the length of the second guide aperture beyond the another distally facing surface.

10. The parallel spacer of claim 8, wherein the first protrusion is configured to fit snugly within at least one of a drill guide or tissue protector to orient the parallel spacer with respect to the drill guide or tissue protector.

11. The parallel spacer of claim 1, wherein the second guide portion includes a second protrusion that includes the distal surface of the second guide portion and that extends distally past another distally facing surface of the parallel spacer, the second guide aperture extending through the second protrusion.

12. A parallel spacer for parallel spacing of a plurality of guiding elements during surgery, comprising:
    a first guide portion that defines a first guide aperture extending through the first guide portion between an opening in a proximal surface and an opening in a distal surface of the first guide portion, the first guide aperture being sized to receive an elongated guiding element and hold a first orientation of the first guide portion with respect to the guiding element, the first guide portion including a first protrusion that includes the distal surface of the first guide portion, the first guide aperture extending through the first protrusion; and
    a second guide portion that defines a guide channel extending portion between an opening in a proximal surface and an opening in a distal surface of the second guide portion and having an open side connecting the openings in the proximal and distal surfaces of the second guide portion, which channel is configured and dimensioned to receive and hold an access needle parallel to the first orientation, and which open side is configured and dimensioned to enable the access needle to be extracted radially from the channel, wherein the second guide portion includes a second protrusion that includes the distal surface of the second guide portion, such that the first and second protrusions define a gap therebetween.

\* \* \* \* \*